(12) United States Patent
Del Rio et al.

(10) Patent No.: US 7,537,524 B2
(45) Date of Patent: May 26, 2009

(54) COUPLING OF DRIVER/DRIVEN SHAFTS OF A MOTOR AND THRUST ISOLATION

(75) Inventors: Eddy H. Del Rio, Royal Palm Beach, FL (US); Douglas A. Perry, Palm Beach Gardens, FL (US)

(73) Assignee: The Anspach Effort Inc, Palm Beach, FL (US)

( * ) Notice: Subject to any disclaimer, the term of this patent is extended or adjusted under 35 U.S.C. 154(b) by 561 days.

(21) Appl. No.: 11/117,591

(22) Filed: Apr. 28, 2005

(65) Prior Publication Data

US 2005/0245318 A1  Nov. 3, 2005

Related U.S. Application Data

(60) Provisional application No. 60/567,188, filed on Apr. 30, 2004.

(51) Int. Cl.
*F16D 3/00* (2006.01)
*B25B 13/46* (2006.01)
*A61B 17/32* (2006.01)

(52) U.S. Cl. ............... 464/139; 464/180; 173/29; 606/180

(58) Field of Classification Search ............ 464/70, 464/85, 87, 120, 123, 124, 139, 141, 180, 464/901; 173/29, 205, 162.1
See application file for complete search history.

(56) References Cited

U.S. PATENT DOCUMENTS

| 2,386,754 | A | * | 10/1945 | Sayder | 464/124 |
| 5,261,233 | A | * | 11/1993 | Kishi | 415/123 |
| 2004/0101225 | A1 | * | 5/2004 | Del Rio et al. | 384/553 |

* cited by examiner

*Primary Examiner*—Victor MacArthur
(74) *Attorney, Agent, or Firm*—Norman Friedland

(57) ABSTRACT

The rotary motion created by a motor is transmitted from the drive shaft of the motor to the driven shaft through a pair of diametrically opposed balls fitted into a coupling mechanism attached to the drive shaft and through a pin fitted into holes formed in the opposed balls and through the driven shaft disposed between the opposed balls for eliminating vibration and noise. The thrust loads imposed in the structure supporting the motor is directed to bypass the motor through a bearing supporting the driven shaft through its housing and into the outer housing surrounding the motor. The motor is encased in a cartridge disposed in a central cavity of the outer housing and the cartridge is not rigidly attached to the outer housing so that the thrust loads bypass the motor.

6 Claims, 2 Drawing Sheets ure and a good feel to afford the surgeon the efficacy of the# COUPLING OF DRIVER/DRIVEN SHAFTS OF A MOTOR AND THRUST ISOLATION This application claims the benefits under 35 U.S.C. § 119(e) of the U.S. provisional patent applications 60/567,188 filed on Apr. 30, 2004

RELATED APPLICATIONS

This invention relates to the pneumatic motor entitled SURGICAL PNEUMATIC MOTOR filed as a non-provisional application Ser. No. 11/082,124 on Mar. 16, 2005 and was invented by myself and co-inventor Douglas Perry and identified as and is incorporated herein by reference and is commonly assigned with this application to The Anspach Effort, Inc.

FEDERALLY SPONSORED RESEARCH OR DEVELOPMENT

Not applicable

TECHNICAL FIELD

This invention relates to motors and particularly to the design of the motor and its appurtenances for isolating the thrust loads and coupling the motor to the output shaft so as to attenuate vibration and noise and enhance the life of the motor.

BACKGROUND OF THE INVENTION

Rotary machines typically utilize motors that are powered pneumatically or electrically so as to cause rotation of the output shaft which is utilized for a given purpose, such as powering a drill, saw and the like. As is well known surgical drills are typically hand-held and for its effective use, the surgical drill should be as quiet as possible, free of vibrations and have a good feel to afford the surgeon the efficacy of the motor when used in surgical procedures.

We have found that by utilizing a ball driven member made from elastomer material and including a thrust load path bypassing the motor will provide the feature that fulfils the requirements of the surgeon, namely a satisfactory noise and vibration level and a good feel of the surgical motor. It is contemplated by this invention that the drive shaft driven by the motor will include a coupling that is adapted to receive diametrically opposed balls made from an elastomer material and the balls are interconnected to a driven shaft. The transfer of rotary motion by this method reduces noise and vibration. To further enhance the operation of the motor the thrust loads according to this invention are diverted to bypass the motor so that the motor is designed to accommodate only radial loads. This aspect of the invention in addition to the other features noted above, enhances the life of the motor.

SUMMARY OF THE INVENTION

An object of this invention is to provide an improved motor that is characterized as being quieter, reduced vibrations and extended life.

A feature of this invention is to provide for a motor a pair of diametrically opposed balls made from elastomer material that is secured to a driven shaft and fitted into a coupling mounted on a driving shaft to transmit power from the motor to the driven device powered by the motor.

Another feature of this invention is to provide a thrust path that absorbs the thrust created by the use of the attachment to the motor that bypasses the motor so as to isolate the load whereby the motor is only concerned with the radial loads.

The foregoing and other features of the present invention will become more apparent from the following description and accompanying drawings.

Figure 1:
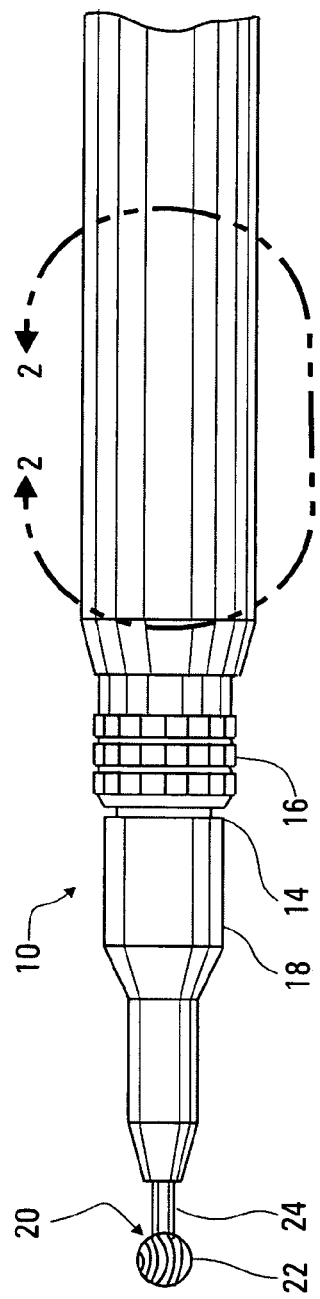
FIG. 1 is a view in elevation illustrating a surgical motor utilizing this invention.
Figure 2:
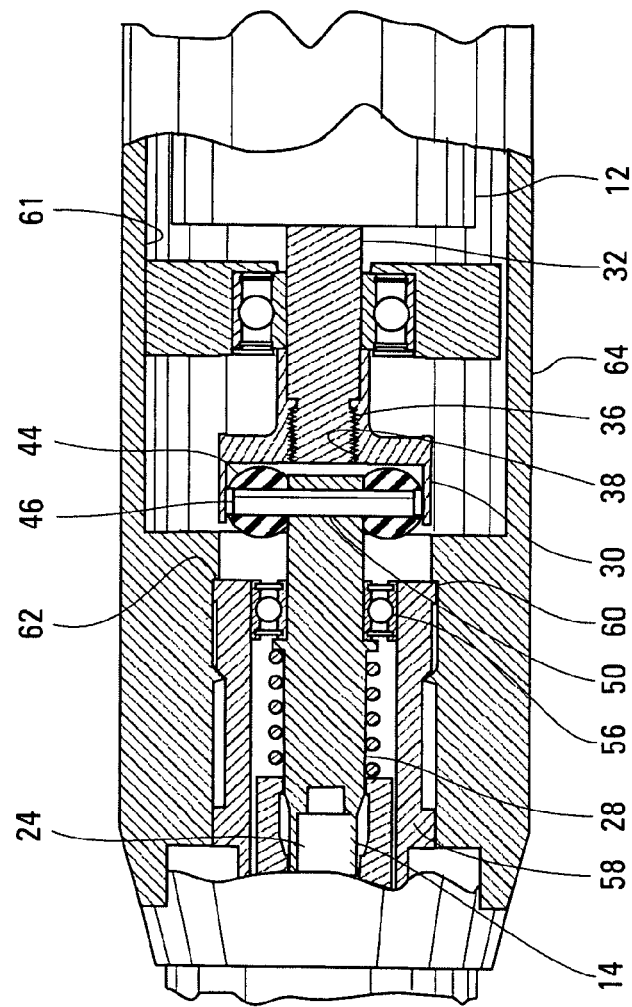
FIG. 2 is an enlarged fragmentary view partly in section and partly in schematic taken along the lines 2-2 of FIG. 1.
Figure 3:
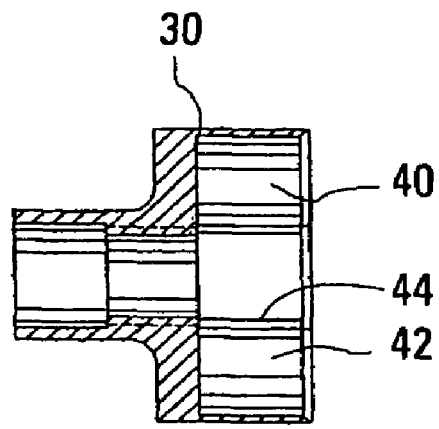
FIG. 3 is a view in schematic of the coupling device of this invention used in the structure depicted in FIG. 1.
Figure 4:
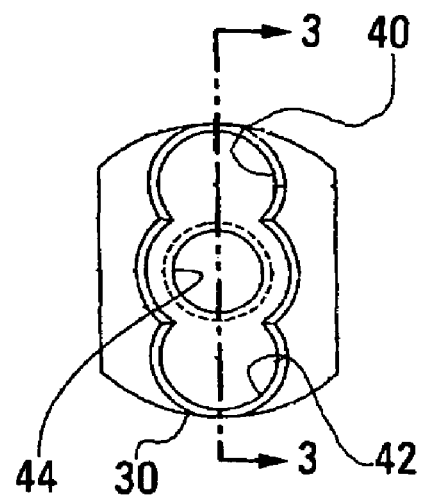
FIG. 4 is an end view of FIG. 3.
Figure 5:
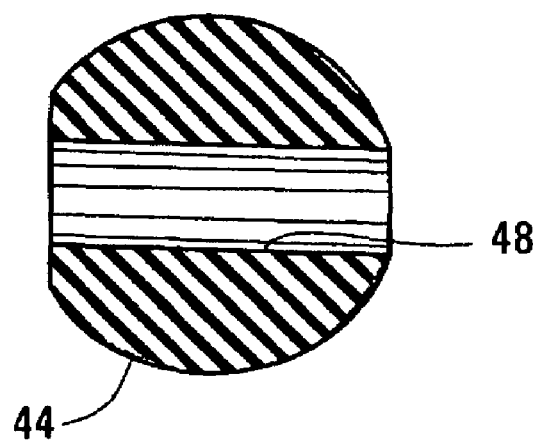
FIG. 5 is a sectional view of the elastomer ball used in the device depicted in FIG. 1.
Figure 6:
FIG. 6 is a plan view of the pin utilized with the ball depicted in FIG. 6 connecting the ball to the driven shaft for transmitting motion from the driver to the driven shafts.

These figures merely serve to further clarify and illustrate the present invention and are not intended to limit the scope thereof.

DETAILED DESCRIPTION OF THE INVENTION

While this invention is being described in its preferred embodiment a surgical drill, as will be understood by those skilled in this art, this invention can by utilized with any type of motor where there is a need to reduce noise and vibrations and to enhance the life of the motor.

The invention can best be understood by referring to all the Figs. illustrating the preferred embodiment of this invention where the surgical instrument generally illustrated by reference numeral 10 includes a motor 12, chucks 14 and 16 that removably mount the attachment 18 and the drill bit 20. The motor and drill bit are well known and for further details reference should be made to commercially available surgical drills of the type available from the assignee of this application or to U.S. Pat. No. 6,752,816 granted to Culp, et al on Jun. 22, 2004 which is incorporated by reference. Suffice it to say that the surgical drill is hand held by the surgeon and has the capability of inserting attachments of different sizes and tools of different sizes and functions. In this preferred embodiment the drill bit 20 includes the cutting spherical tip 22 and shaft 24 with the proximate end fitting into a well known chuck 26 that serves to removably attach it to the driven shaft 28. In accordance with this invention the coupler 30 is affixed to driver shaft 32 rotated by the motor 12 shown in blank. Inasmuch as the type of motor, be it pneumatic or electric, is not important to the invention, for the sake of convenience and simplicity details thereof are omitted here from and details to a motor should be made to the Culp et al patent, supra. The important aspect of this invention is the manner in which the rotary motion from the drive shaft is transmitted to the driven shaft.

The coupler 30 includes inner threads 36 that thread onto the outer threads 38 formed on the outer periphery on the drive shaft 32 so that coupler 30 is powered by the motor 12. Coupler 30 includes a pair of diametrically opposed cup-like shaped apertures or recesses 40 and 42, preferably spherical in shape, for receiving the balls 44 as will be described hereinbelow. A central bore 44 formed in the coupling 30 receives the driver shaft 32. Balls 44 (two), shown enlarged, are made from an elastomer material such as commercially available rubber composition, such as Santroprene® rubber or Viton® made by Dupont Dow, and are fitted into spherically shaped apertures or recesses 40 and 42 and the pin 46 is fitted through the central bore 48 formed in each of the two balls 44 and through a complementary hole 50 formed in driven shaft 28. The pin 46 fitted into the respective central bores 48 in the two diametrically opposed balls 44 tie the coupling 30 to shaft 28 and hence, since coupling 30 is tied to the drive shaft 32 the rotary motion created by motor 12 is transmitted to the driven shaft 28 via the elastomeric balls 44. By virtue of this connection, the noise and vibrations of the surgical instrument was significantly reduced.

The next portion of this description is concerned with the thrust imposed on the unit when the drill bit is urged against an object in the course of the drilling operation. This thrust load is transmitted into the surgical instrument through shaft 24, then into the chuck 26 where it is transmitted to the bearing 56 that serves to rotary support driven shaft 28. Bearing 56 is contained in housing 58 which carries a flange 60 formed on the end thereof. Flange 60 bears against a complementary shoulder 62 that is formed in the outer housing 64 of the surgical instrument. According to this invention, motor 12 is inserted into a cartridge supported within a central cavity 61 in outer housing 64 but is not rigidly tied to the outer housing 64. Hence, the thrust load instead of being transmitted through the motor which is the typical design, the thrust load is transmitted directly into the outer housing 64 and bypassing the motor 12. This feature not only allows the designer to consider the radial loads imposed on the motor, but it also has the propensity of enhancing the life of the motor.

Although this invention has been shown and described with respect to detailed embodiments thereof, it will be appreciated and understood by those skilled in the art that various changes in form and detail thereof may be made without departing from the spirit and scope of the disclosed invention.

The invention claimed is:

1. A motor for generating rotary motion comprising,
a driver shaft and a driven shaft,
a coupler attached to said driver shaft, said coupler including diametrically opposed recesses formed at one end thereof,
a pair of balls each of which are mounted in said recesses, said balls made from an elastomer material,
a pin extending through openings formed in each of said balls and a complementary opening formed in said driven shaft to rigidly connect said pair of balls to said driven shaft, whereby rotary motion of said driver shaft is transmitted to said driven shaft.

2. A motor as claimed in claim 1 wherein said coupling includes attachment mechanism formed in said coupling, and means for connecting said driver shaft to said attachment mechanism.

3. A surgical instrument having an outer case,
a motor mounted in a cavity formed in said outer case,
said motor having a driver shaft extending from one end thereof,
a coupling mechanism rigidly secured to said driver shaft and rotating therewith,
a driven shaft,
said coupling mechanism including a pair of diametrically disposed recesses formed therein so that each of said pair of diametrically disposed recesses are located on opposite sides of said driven shaft, each of said pair of recesses being spherically shaped,
a pair of spherically shaped balls mounted in said pair of diametrically opposed recesses, each of said pair of spherically shaped balls being made from an elastomeric material,
a pin extending through a central bore formed in each of said pair of spherically shaped balls and a through hole formed in said driven shaft, whereby said motor rotates said driver shaft and said driver shaft transmits said motion to said driven shaft by said pair of spherically shaped balls and said pin.

4. A motor for generating rotary motion,
an outer housing,
said motor disposed in said outer housing,
a driver shaft attached to said motor,
a driven shaft,
a coupler attached to said driver shaft, said coupler including diametrically opposed recesses formed at one end thereof,
a pair of balls mounted in said recesses, said balls made from an elastomer material,
a pin extending through openings formed in said ball and a complementary opening formed in said driven shaft to rigidly connect said pair of balls to said driven shaft, whereby the rotary motion of said driver shaft is transmitted to said driven shaft through said coupling, said pair of balls and said pin,
a working instrument attached to said driven shaft that creates thrust loads to said housing,
a bearing supporting said driven shaft and having a flange,
a shoulder formed in said housing bearing against said flange, whereby the thrust loads are transmitted through said bearing and to said outer housing, by-passing said motor.

5. A surgical instrument having a hand-held outer housing and a shoulder depending from said outer housing,
a motor disposed in said outer housing,
a driver shaft extending from one end of said motor,
a coupler affixed to said driver shaft, said coupler having a pair of diametrically opposed recesses,
a pair of balls, each of which is made from an elastomer material and is supported in each of said pair of recesses and each of said balls having a central through bore,
a driven shaft for driving a surgical tool,
a bearing mounted in said housing for supporting said driven shaft, said bearing including a flange portion bearing on said shoulder,
wherein thrust loads transmitted from said surgical tool are transmitted through said flange and said shoulder and said outer housing by-passing said motor.

6. A surgical instrument as claimed in claim 5 wherein each of said recesses and said pair of balls are spherically shaped.

* * * * *